(12) United States Patent
Su et al.

(10) Patent No.: US 9,505,004 B2
(45) Date of Patent: Nov. 29, 2016

(54) DEVICE FOR CONTROLLING THERMAL CONVECTION VELOCITY OF BIOCHEMICAL REACTION AND METHOD FOR THE SAME

(75) Inventors: Chen Su, Taichung (TW); Ping-Hua Teng, Taichung (TW); Chien-Chung Jeng, Taichung (TW)

(73) Assignee: GeneReach Biotechnology Corp., Taichung (TW)

( * ) Notice: Subject to any disclaimer, the term of this patent is extended or adjusted under 35 U.S.C. 154(b) by 85 days.

(21) Appl. No.: 14/383,905

(22) PCT Filed: Mar. 9, 2012

(86) PCT No.: PCT/CN2012/072125
§ 371 (c)(1),
(2), (4) Date: Oct. 31, 2014

(87) PCT Pub. No.: WO2013/131274
PCT Pub. Date: Sep. 12, 2013

(65) Prior Publication Data
US 2015/0044726 A1   Feb. 12, 2015

(51) Int. Cl.
| C12M 1/24 | (2006.01) |
| B01L 7/00 | (2006.01) |
| C12M 1/34 | (2006.01) |
| C12Q 1/68 | (2006.01) |

(52) U.S. Cl.
CPC .............. B01L 7/525 (2013.01); C12M 41/12 (2013.01); C12Q 1/686 (2013.01); *B01L 2300/185* (2013.01); *B01L 2400/0445* (2013.01); *B01L 2400/082* (2013.01)

(58) Field of Classification Search
CPC ....... B01L 7/525; C12M 41/12; C12Q 1/686
See application file for complete search history.

(56) References Cited

U.S. PATENT DOCUMENTS

| 2,013,109 A * | 9/1935 | Reynolds .............. F16F 15/173 226/181 |
| 2,770,707 A * | 11/1956 | Jordan ...................... B01L 7/00 219/521 |
| 5,616,301 A * | 4/1997 | Moser ....................... B01L 7/52 422/562 |
| 6,403,037 B1 * | 6/2002 | Chang ..................... B01L 3/502 250/238 |
| 6,677,151 B2 * | 1/2004 | Sandell ..................... B01L 7/52 422/65 |
| 7,255,833 B2 * | 8/2007 | Chang .................. B01J 19/0093 422/417 |
| 2012/0207646 A1 * | 8/2012 | Osaka .................. G01N 35/025 422/68.1 |
| 2012/0244047 A1 * | 9/2012 | Teng .......................... B01L 9/06 422/562 |
| 2012/0244048 A1 * | 9/2012 | Teng .......................... B01L 9/06 422/562 |

\* cited by examiner

*Primary Examiner* — Jill Warden
*Assistant Examiner* — Brittany Fisher
(74) *Attorney, Agent, or Firm* — CKC & Partners Co., Ltd.

(57) ABSTRACT

The present disclosure is related to a device for controlling thermal convection velocity of a biochemical reaction. The thermal convection velocity controlling device includes a base body for disposing a tube which is movable, wherein the tube is filled with a buffer of the biochemical reaction; a heating source located at a bottom of the tube or at a side of the tube to heat the buffer; and a flow rate adjusting apparatus for controlling a thermal convection flow direction of the buffer in the tube, whereby the flow rate adjusting apparatus changes a flow velocity and a flow time of the buffer. The present disclosure is also related to a method for controlling thermal convection velocity of a biochemical reaction using the device.

5 Claims, 7 Drawing Sheets

Fig. 3 a). At least one buffer of the biochemical reaction is filled in the tube b). The tube which is movable is disposed on the base body c). The bottom of the tube or the side of the tube is heated by the heating source d). The temperature of the top of the tube is decreased by outside air and the thermal convection circulation is generated in the buffer e). In accordance with the single nucleic acid amplification reaction period needed in the buffer, the tube at a tilt angle is adjusted for controlling the flow direction of the buffer, and therefore the flow velocity and the flow time of the buffer are changed

DEVICE FOR CONTROLLING THERMAL CONVECTION VELOCITY OF BIOCHEMICAL REACTION AND METHOD FOR THE SAME

CROSS-REFERENCE TO RELATED APPLICATION

This application is a continuation of International application No. PCT/CN2012/072125, filed on Mar. 9, 2012, the content of which is incorporated herein by reference.

BACKGROUND

Technical Field

The present disclosure relates to a method for enhancing the efficiency of nucleic acid amplification. More particularly, the present disclosure relates to a device used in polymerase chain reaction (PCR), which is for enhancing the efficiency of nucleic acid amplification by controlling the thermal convection flow rate of the buffer in the tube to increase the single thermal convection circulation period.

Description of Related Art

For genetic research such as genetics and molecular biology or the detection of animal and plant diseases, it needs to amplify a few copies of nucleic acids by nucleic acid amplification, such as polymerase chain reaction (PCR), from a small amount of nucleic acid samples to the amount which can be detected in a short time. The nucleic acid amplification products can be further hybridized to nucleic acid probes conjugated with fluorescent, radioactive substances or colorimetric enzyme, thus producing fluorescence, radiation image or color reaction.

The aforementioned process of the polymerase chain reaction includes three main steps: denaturation, annealing reaction and extension reaction, and the required reaction temperature of the three main steps are different. Nowadays the sample of commercialized PCR amplification technology includes the template DNA far amplification, the oligonucleotide primers which are complementary to particular sequences of each strand of template DNA, thermostable DNA polymerase, and deoxy-ribonucleoside triphosphate (dNTP), then the reaction repeats heating and cooling the sample, and the sample is circulated between different temperatures to amplify the particular part of template DNA nucleic acid sequence.

In the aforementioned denaturation, the sample is heated to high temperatures, causing the double-stranded template DNA to be separated into single-stranded DNA; in the annealing reaction, the sample is cooled to a lower temperature, allowing annealing of the primers to the single-stranded DNA templates which are formed in denaturation to form a DNA-primer hybrid; in the extension reaction, the sample is maintained at an appropriate temperature, and the primer of the DNA-primer hybrid can be extended to synthesize a new DNA strand complementary to each of the DNA template through the action of DNA polymerase; the DNA sequences between the binding sites of the forward primer and the reverse primer can be replicated in each cycle consisting of three main steps.

The temperature of the sample tube of conventional PCR reaction apparatus is controlled by heat conduction, for example, the PCR sample tube is in contact with a solid metal block of high thermal conductivity, changing the temperature of the sample tube by heating and cooling to reach the required temperature of the PCR sample tube. The majority of sample tubes are held in a vertical position during heating, and the metal block with thermal conductivity is disposed at the bottom of the sample tube to generate temperature difference in the tube to generate thermal convection circulation phenomenon in the internal buffer. However, the effectiveness of the nucleic acid amplification will be influenced by the thermal convection velocity of buffer. When the thermal convection velocity is too fast, it will cause the single thermal convection circulation period to be less than the single nucleic acid amplification period, resulting in the nucleic acid amplification to be incomplete. By contrast, when the thermal convection velocity is too slow, it will increase the required spent time of nucleic acid amplification. The flow rate of the buffer will be influenced by multiple factors, such as the compositions of the buffer solution and the temperature differences between the top of the tube and the bottom of the tube. Therefore, in order to change the flow rate of the buffer, the currently practiced manners include adding substances into the buffer to change the viscosity of buffer, or controlling the temperature differences between the top of the tube and the bottom of the tube. Although these manners can indeed change the thermal convection rate, the thermal convection rate is often not effectively manipulated due to these manners are very difficult to control.

SUMMARY

As the previously stated, the disadvantages of prior art includes the currently practiced PCR reaction apparatus described above. The effectiveness of nucleic acid amplification will be influenced by thermal convection velocity of the buffer. In order to change the flow rate of the buffer, the currently practiced manners include adding substances into the buffer to change the viscosity of buffer, or controlling the temperature differences between the top of the tube and the bottom of the tube. However, the thermal convection rate is often not effectively manipulated due to these manners are very difficult to control. In view of solving the disadvantages above, the present disclosure provides a device for controlling thermal convection velocity of a biochemical reaction and method for the same.

The present disclosure relates to a device for controlling thermal convection velocity of a biochemical reaction and method for the same. The device for controlling thermal convection velocity of a biochemical reaction includes a base body for disposing a tube which is movable, wherein the tube is filled with a buffer for the biochemical reaction; a heating source located at a bottom of the tube or at a side of the tube to heat the buffer; and a flow rate adjusting apparatus for controlling a thermal convection flow direction of the buffer in the tube, whereby the flow rate adjusting apparatus changes a flow velocity and the flow time of the buffer, hence a single thermal convection circulation period of the buffer is equal to or longer than a single nucleic acid amplification period of the biochemical reaction.

The method of above biochemical reaction includes the following steps:

a). filling a buffer of a biochemical reaction in the tube;

b). disposing the tube which is movable on the base body;

c). heating the bottom of the tube or the side of the tube by the heating source;

d). decreasing a temperature of the top of the tube by outside air and generating a thermal convection circulation in the buffer; and e). In accordance with the single nucleic acid amplification period needed in the buffer, adjusting the tube at a tilt angle for controlling the flow direction of the buffer, and therefore changing the flow velocity and the flow time of the buffer.

The main purpose of the present disclosure is controlling the thermal convection flow direction of the buffer in the tube with the flow rate adjusting apparatus to change the flow velocity and time of the buffer, to make the single thermal convection circulation period of the buffer equal to or longer than the single nucleic acid amplification period of the biochemical reaction. Hence, the efficiency of the nucleic acid amplification is improved.

DETAILED DESCRIPTION

Reference will now be made in detail to the present embodiments of the present disclosure, examples of which are illustrated in the accompanying drawings. That must be explained first, the elements of the embodiments are drawn for easily explaining the ratio, size, and degrees of deformation and position shift, and are not drawn to scale. Wherever possible, the same reference numbers are used in the drawings and the description to refer to the same or like parts.

Figure 5:
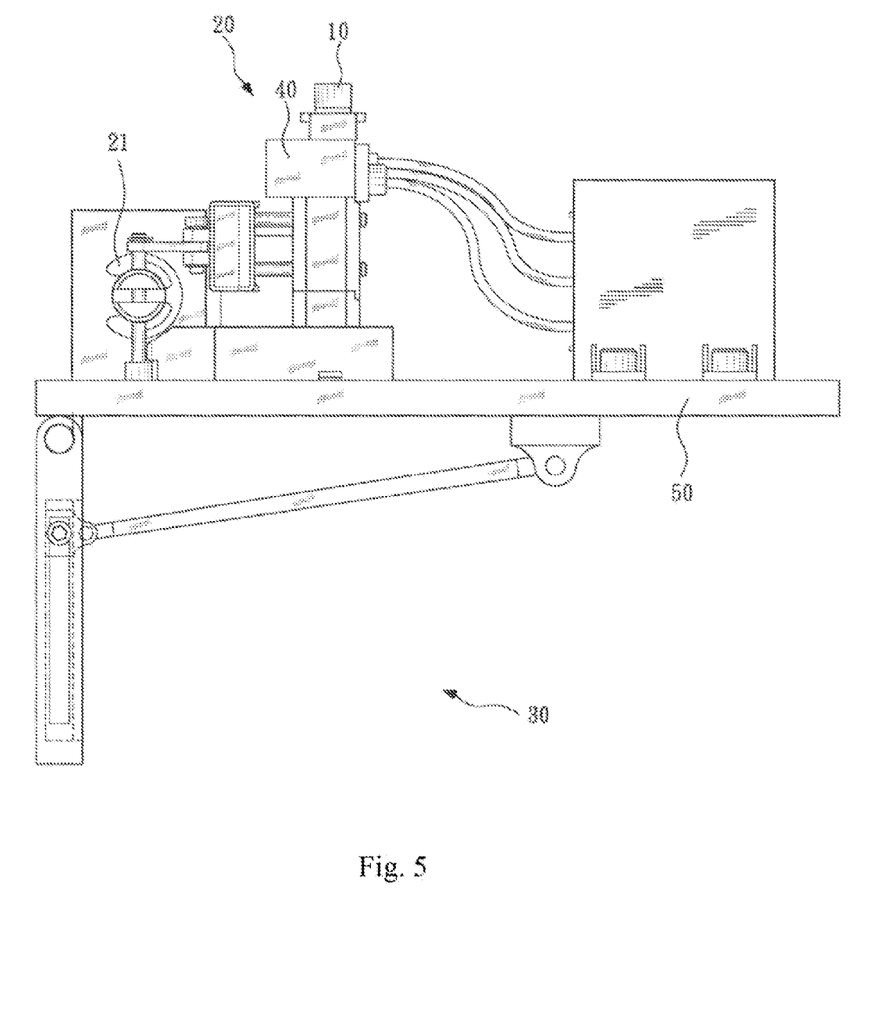
FIG. 5 is a schematic diagram of a using state before adjusting an angle of the tube according to one embodiment of the present disclosure.

The present disclosure relates to a device for controlling thermal convection velocity of a biochemical reaction and method for the same. That must be explained first, each component and setting in the drawings are only for easily explaining the present disclosure. The present disclosure covers variations of the reaction apparatus and is not limited to the illustration shown in the drawings. In FIG. 5, to achieve the purpose that the present disclosure can control the thermal convection velocity required for the biochemical reaction, the elements related to the main technical contents of the present disclosure include a tube 10, a heating source 20, and a flow rate adjusting apparatus 30.

The tube 10, provided for nucleic acid extraction, is filled with at least one buffer 11 of the biochemical reaction and at least one fluorescent substance. The buffer 11 can be the buffer of polymerase chain reaction, wherein depending on various quantitative analysis methods, the buffer and fluorescent substances can be different, for example, DNA intercalation reagents (it can be EtBr, SYBR Green, etc.), turbidity reagents (it can be magnesium Pyrophosphate), fluorescent dyes (it can be FAM, Cy3 and Cy5), visible light detection or calorigenic reagent.

Figure 7:
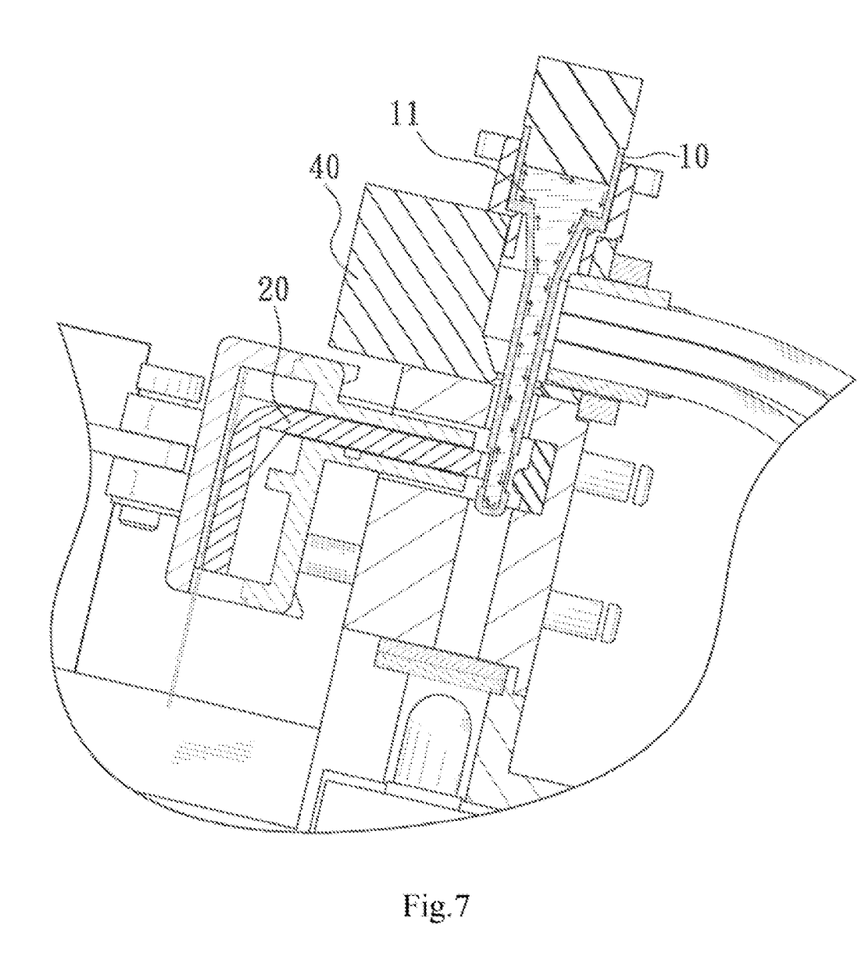
FIG. 7 is a schematic diagram of an operation of the tube at a tilt angle according to one embodiment of the present disclosure.

The heating source 20 is located at a bottom of the tube 10 or at a side thereof. The heating source 20 can be a thermally conductive sheet, and is for providing thermal conductive effectiveness with a heating source, or a heating source generally used in biochemical reactions, wherein the heating source 20 can be any manner which can achieve the same purpose of heating the tube 10. The heating source 20 can be controlled by a driving apparatus 21 to come in contact with the tube 10, thus the temperature of the buffer 11 (as shown in FIG. 7) in the tube 10 is the required temperature for nucleic acid amplification, wherein the bottom of the tube 10 is heated by the heating source 20 to increase the temperature of the buffer 11 to reach the required temperature for DNA denaturation, for which the optimal temperatures are 90 degrees Celsius to 99 degrees Celsius for current nucleic acid amplification. Furthermore, the temperature of the top of the tube 10 should be decreased below the required temperature for the primer annealing reaction. Therefore, the temperature difference of the buffer 11 between two ends of the tube 10 could be established to generate thermal convection.

The flow rate adjusting apparatus 30 is for controlling the flow direction of the thermal convection of the buffer 11 in the tube 10. The flow velocity and time of the buffer 11 are changed by controlling the flow direction of the buffer 11, hence the single thermal convection circulation period is equal to or longer than the single nucleic acid amplification period of the biochemical reaction to enhance the effectiveness of the nucleic acid amplification.

After understanding these main components and principles of the reaction apparatus, the operations and, principles of the present disclosure are described in detail as follows.

Figure 4:
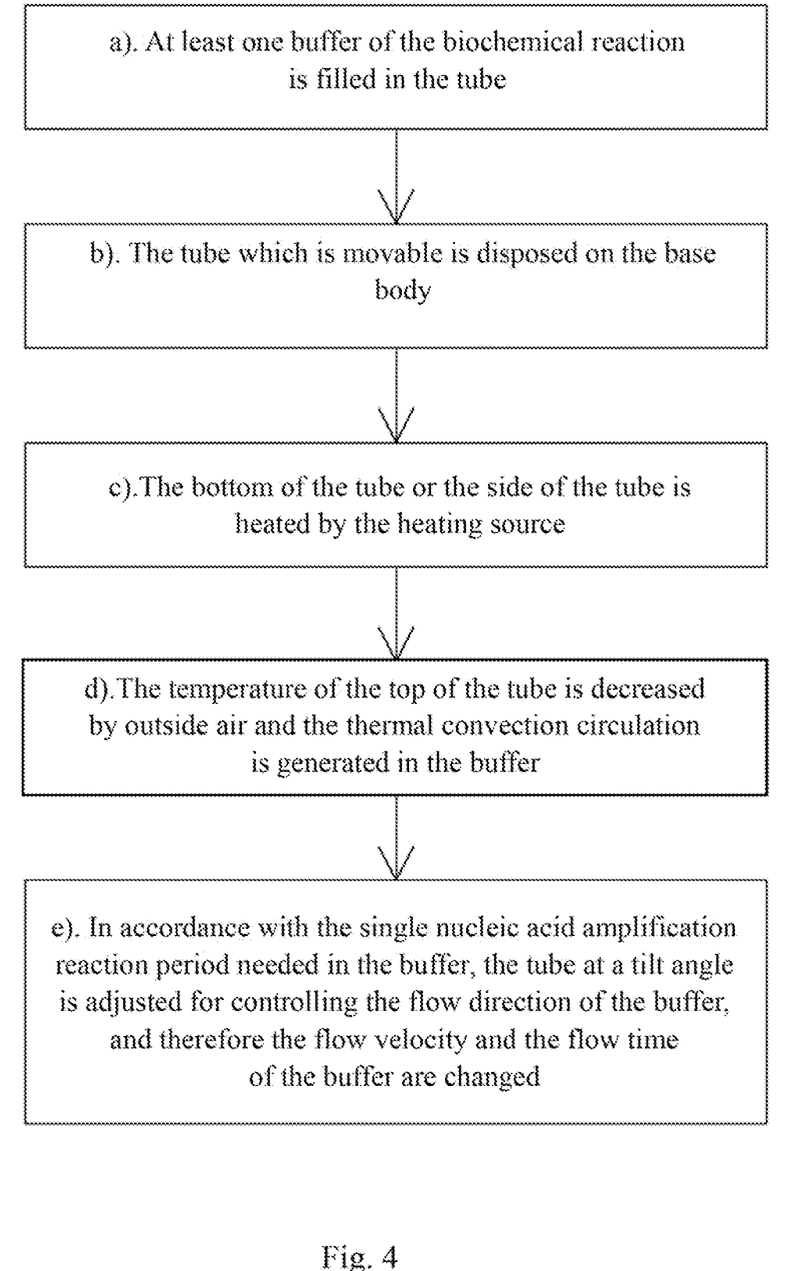
FIG. 4 is a flow chart of operation of the present disclosure.
Figure 6:
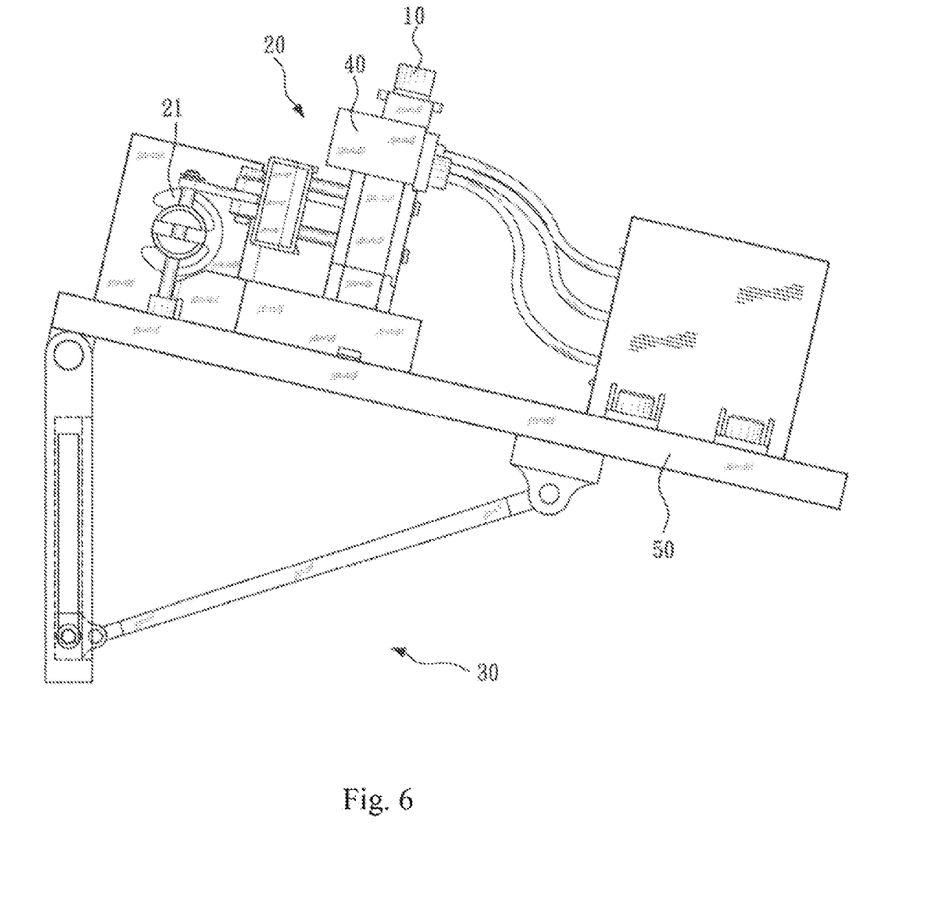
FIG. 6 is a schematic diagram of a using state after adjusting an angle of the tube according to one embodiment of the present disclosure.

In FIG. 4 to FIG. 6, the protocol of the present disclosure includes following steps:

a). at least one buffer 11 of the biochemical reaction is filled in the tube 10;

b). the tube 10 which is movable is disposed on the base body 40;

c). the bottom of the tube 10 or the side of the tube 10 is heated by the heating source 20;

d). the temperature of the top of the tube 10 is decreased by outside air and a thermal convection circulation is generated in the buffer 11:

e). In accordance with the single nucleic acid amplification period needed in the buffer 11, the tube 10 is adjusted at a tilt angle for controlling the flow direction of the buffer 11, and therefore the flow velocity and the flow time of the buffer 11 are changed.

FIG. 5 to FIG. 7 are schematic diagrams of the reaction apparatus in action according to one embodiment of the present disclosure. The base body 40 is disposed on a working bench 50, wherein the base body 40 is provided for disposing the tube 10 which is movable and the working bench 50 can be a flat plate. The flow rate adjusting apparatus 30 is connected to the working bench 50 for controlling the tilt angle of the working bench 50 and the base body 40. As the illustrations, the flow rate adjusting apparatus 30 can drive the working bench 50 to adjust the angle through a connecting rod. The flow rate adjusting apparatus 30 also can be other structures which are used to adjust the angle of the working bench 50, for example, gear motor-mediated movement.

Through the control of the driving apparatus 21, the heating source 20 comes in contact with the tube 10 to heat the tube 10. When the temperature of the bottom of the tube 10 is increased, DNA in the buffer 11 will be denatured, when the buffer 11 flows to the top of the tube 10 to allow the buffer 11 to cool down, DNA in the buffer 11 will begin to replicate. Therefore, PCR amplification can be done in the buffer 11 during the circulation between the heating and cooling zones.

Figure 1:
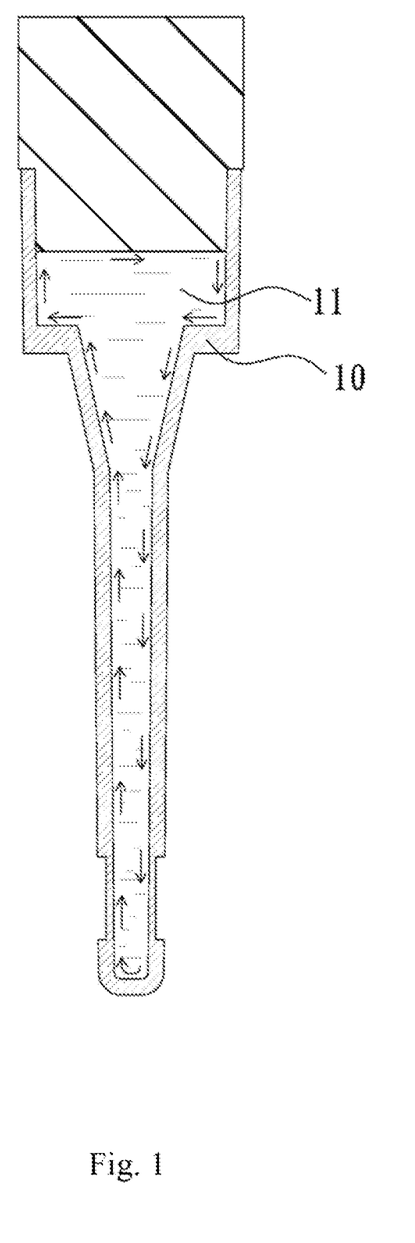
FIG. 1 is a schematic diagram of the thermal convection circulation in the sample tube which is in a vertical position during the biochemical reaction.
Figure 2:
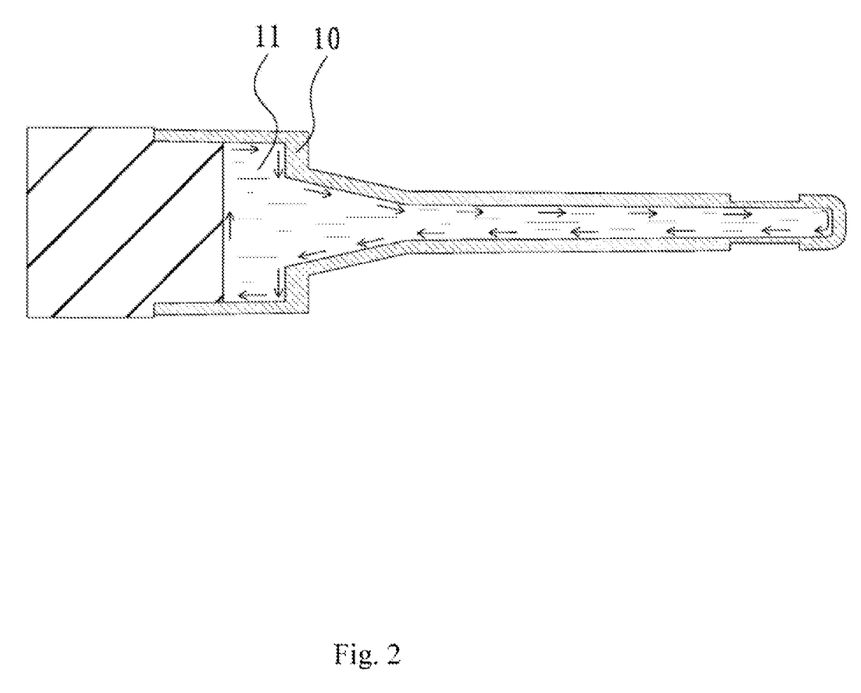
FIG. 2 is a schematic diagram of the thermal convection circulation in the sample tube which is in a horizontal position during the biochemical reaction.
Figure 3:
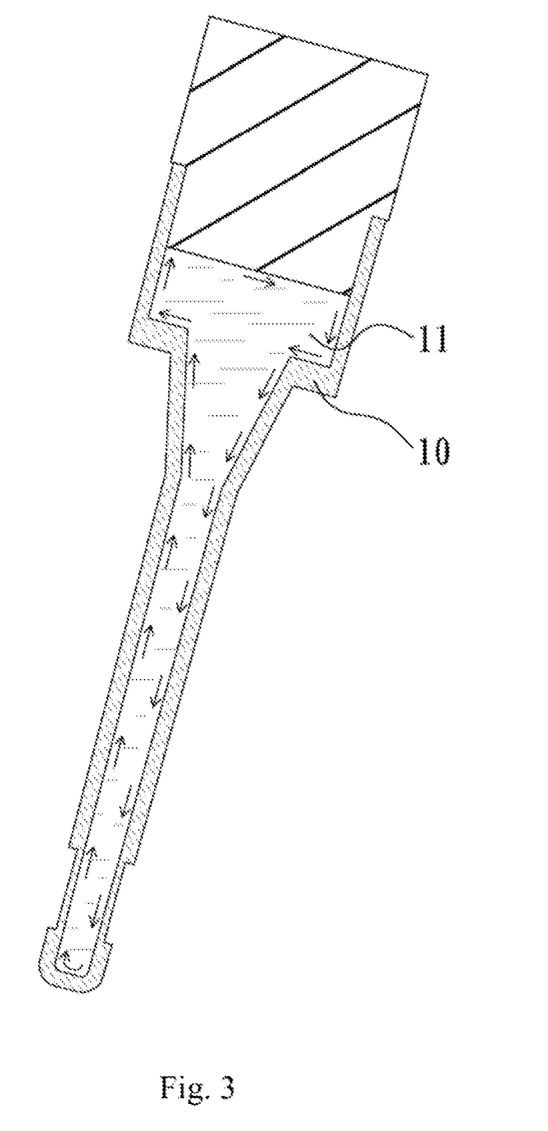
FIG. 3 is a schematic diagram of the thermal convection circulation in the sample tube which is in an inclined position during the biochemical reaction.

According to the above arrangement of configuration, in accordance with the required thermal convection velocity of the buffer 11, the base body 40 can drive the tube 10 to adjust the tilt angle to change the ratio of the change of the tube 10 in the vertical direction to the change of the tube 10 in the horizontal direction, thus the flow direction of the buffer 11 is changed. FIG. 1 to FIG. 3 are schematic diagrams of the tube 10 which is in a vertical, horizontal and inclined position, respectively. When the direction of the tube 10 is positioned closer to the vertical direction, the flow rate of the buffer 11 is higher. By contrast, when the direction of the tube 10 is positioned closer to the horizontal direction, the flow rate of the buffer 11 is lower. After experimental operation of the present disclosure, the angle between the arranged angle of the tube 10 and the vertical line over the ground can be greater than 0° and smaller than 45°, wherein the optimum angle is greater than 0° and smaller than 15° according to the optimal thermal convection velocity of the buffer 11 which is required in current nucleic acid amplification.

The contact area between the wall of the tube 10 and the buffer 11 flowing upward can be increased in thermal convection when the tube 10 is placed in the tilt angle. Thus, this can reduce the velocity and time of thermal convection circulation of the buffer 11, compared to the results in the tube 10 positioned in the vertical direction. Through this, the single thermal convection circulation period of the buffer 11 is equal to or longer than a single nucleic acid amplification period of the biochemical reaction. This could avoid the excessive circulation velocity in the single thermal convection, which may result in the single thermal convection circulation period of the buffer 11 to be shorter than the single nucleic acid amplification period of DNA in buffer 11, influencing the results of nucleic acid amplification. Therefore, the present disclosure can effectively enhance the effectiveness of nucleic acid amplification.

In other embodiment of the present disclosure, in order to fix the tube 10 in the tilt angle, the flow rate adjusting apparatus 30 can be a bearing base (not shown) which is placed on the base body 40 and for holding the tube 10, and the bearing base (not shown) is capable of adjusting a tube angle on the base body 40, or an inclined plane (not shown) for holding the tube 10 can be included on the base body 40. In addition to all of the above methods, the tube 10 can be clamped by a hand-held tube holder, and the tube 10 can be tilted manually to achieve the same purpose described above.

Although the present disclosure has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present disclosure without departing from the scope or spirit of the invention. In view of the foregoing, it is intended that the present disclosure cover modifications and variations of this disclosure provided they fall within the scope of the following claims.

What is claimed is:

1. A thermal convection velocity controlling method for applying to a device for controlling thermal convection velocity of a biochemical reaction, comprising the following steps:
   a). filling a buffer of a biochemical reaction in a tube for performing an convective polymerase chain reaction therein;
   b). disposing the tube which is movable on a base body; and
   c). performing the convective polymerase chain reaction by:
      1). heating a bottom of the tube or an end side of the tube by a heating source;
      2). decreasing a temperature of a top of the tube by outside air and generating a thermal convection circulation in the buffer; and
      3). adjusting the tube at a tilt angle using a flow rate adjusting apparatus, which is a tilting load-bearing device connected to the base body, thus controlling a flow direction of the buffer in accordance with a single nucleic acid amplification period needed in the buffer, and therefore changing a flow velocity and a flow time of the buffer, thereby completing: (i) denaturation, (ii) annealing, and (iii) extension.

2. The method of claim 1, wherein the tilt angle is greater than 0° and smaller than 45°.

3. The method of claim 1, wherein the tilt angle is greater than 0° and smaller than 15°.

4. A thermal convection velocity controlling method for applying to a device for controlling thermal convection velocity of a biochemical reaction, comprising the following steps:
   a) disposing a base body on a working bench, wherein the working bench has a top surface and a bottom surface, and is pivotally connected at one end to a support structure, and wherein a connecting rod is pivotally connected to the bottom surface of the working bench at a first end of the connecting rod and slidably connected to the support structure at a second end of the connecting rod;
   b) filling a buffer of a biochemical reaction in a tube;
   c) disposing the tube which is movable on a base body;
   d) heating a bottom of the tube or a side of the tube by a heating source;
   e) decreasing a temperature of a top of the tube by outside air and generating a thermal convection circulation in the buffer; and
   f) adjusting the tube at a tilt angle by sliding the second end of the connecting rod along the support structure from an upper position to a lower position, thus controlling a flow direction of the buffer in accordance with a single nucleic acid amplification period needed in the buffer, and therefore changing a flow velocity and a flow time of the buffer.

5. A thermal convection velocity controlling method for applying to a device for controlling thermal convection velocity of a biochemical reaction, comprising the following steps:
   a) filling, a buffer of a biochemical reaction in a tube;
   b) disposing the tube which is movable on a base body;
   c) heating a bottom of the tube or a side of the tube by a heating source;
   d) decreasing a temperature of a top of the tube by outside air and generating a thermal convection circulation in the buffer; and
   e) adjusting the tube at a tilt angle using a flow rate adjusting apparatus, characterized in that the flow rate adjusting apparatus is a bearing base which is placed on the base body and for holding the tube, and the bearing base adjusts a tube angle on the base body, thus for controlling a flow direction of the buffer in accordance with a single nucleic acid amplification period needed in the buffer, and therefore changing a flow velocity and a flow time of the buffer.

\* \* \* \* \*